United States Patent [19]

Sumitani et al.

[11] Patent Number: 5,365,001
[45] Date of Patent: Nov. 15, 1994

[54] METHOD FOR PREPARING DIALKYLNAPHTHALENE

[75] Inventors: Koji Sumitani, Koganei; Keizo Shimada; Seiji Itoh, both of Iwakuni; Kimihiko Sato; Risuke Suzuki, both of Matsuyama; Akio Namatame, Tokyo, all of Japan

[73] Assignee: Teijin Limited, Japan

[21] Appl. No.: 39,067

[22] PCT Filed: Aug. 6, 1992

[86] PCT No.: PCT/JP92/01006

§ 371 Date: Apr. 8, 1993

§ 102(e) Date: Apr. 8, 1993

[87] PCT Pub. No.: WO93/02995

PCT Pub. Date: Feb. 18, 1993

[30] Foreign Application Priority Data

| Aug. 8, 1991 | [JP] | Japan | 3-222440 |
| Sep. 4, 1991 | [JP] | Japan | 3-250341 |
| Sep. 5, 1991 | [JP] | Japan | 3-252793 |
| Aug. 6, 1992 | [JP] | Japan | 4-057950 |

[51] Int. Cl.$^5$ .................. C07C 5/00; C07C 15/24
[52] U.S. Cl. .................. 585/411; 585/379; 585/418; 585/419
[58] Field of Search ........... 585/379, 407, 410, 411, 585/418, 419; 502/61, 66

[56] References Cited

U.S. PATENT DOCUMENTS

| 3,244,758 | 4/1966 | Eberhardt | 260/668 |
| 3,431,219 | 3/1969 | Argauer et al. | 252/455 |
| 3,931,348 | 1/1976 | Taniguchi et al. | 260/668 F |
| 3,954,896 | 5/1976 | Shima et al. | 260/668 B |
| 4,392,989 | 7/1983 | Chu et al. | 252/455 Z |
| 4,458,025 | 7/1984 | Lee et al. | 502/66 |
| 4,623,632 | 11/1986 | Lambert et al. | 502/74 |
| 4,824,816 | 4/1989 | Trowbridge et al. | 502/66 |
| 4,873,386 | 10/1989 | Hagen et al. | 585/471 |
| 4,985,384 | 1/1991 | Gilson | 502/61 |
| 5,003,122 | 3/1991 | Fellman et al. | 585/467 |
| 5,008,479 | 4/1991 | Abe et al. | 585/320 |
| 5,023,390 | 6/1991 | Abe et al. | 585/320 |
| 5,030,781 | 7/1991 | Sikkenga et al. | 585/320 |

FOREIGN PATENT DOCUMENTS

| 215351 | 3/1987 | European Pat. Off. |
| 430714 | 6/1991 | European Pat. Off. |

(List continued on next page.)

*Primary Examiner*—Asok Pal
*Assistant Examiner*—P. Achutamurthy
*Attorney, Agent, or Firm*—Wenderoth, Lind & Ponack

[57] ABSTRACT

A method for preparing a dialkylnaphthalene in one step by contacting an dialkylbenzene compound with a solid catalyst in a gas or liquid phase in the presence of hydrogen, using a catalyst having composition (I) or (II) below:

(1)

$$(M^1)_a \cdot (M^2)_b \cdot (SiO_2 \cdot XAl_2O_3) \cdot (Al_2O_3)_c \quad (I)$$

(2) Mixture of II-(i) and II-(ii):

$$(M^3)_d \cdot (Al_2O_3) \quad \text{II-(i)}$$

$$(M^4)_e \cdot (SiO_2 \cdot XAl_2O_3) \quad \text{II-(ii)}$$

wherein $M^1$ is a metal selected from the group consisting of metals belonging to group VIII of a periodic table and rhenium;

$M^2$ is a member selected from the group consisting of zinc, gallium, and oxides thereof;

$M^3$ is a metal belonging to group VIII of a periodic table;

$M^4$ is at least one alkali metal; and a, b, c, d, e, and X represent proportions, respectively.

30 Claims, No Drawings

FOREIGN PATENT DOCUMENTS

| | | |
|---|---|---|
| 50-665 | 1/1975 | Japan . |
| 1036 | 1/1975 | Japan . |
| 1037 | 1/1975 | Japan . |
| 50-1269 | 1/1975 | Japan . |
| 50-4655 | 2/1975 | Japan . |
| 12430 | 5/1975 | Japan . |
| 50-17985 | 6/1975 | Japan . |
| 50-22551 | 7/1975 | Japan . |
| 6953 | 1/1976 | Japan . |
| 135756 | 10/1979 | Japan . |
| 48494 | 11/1981 | Japan . |
| 45536 | 3/1985 | Japan . |
| 172937 | 9/1985 | Japan . |
| 188343 | 9/1985 | Japan . |
| 53937 | 3/1987 | Japan . |
| 9942 | 1/1989 | Japan . |
| 9943 | 1/1989 | Japan . |
| 96540 | 4/1990 | Japan . |
| 167237 | 6/1990 | Japan . |
| 500179 | 1/1991 | Japan . |
| 3-251545 | 11/1991 | Japan . |
| 90/03961 | 4/1990 | WIPO . |

METHOD FOR PREPARING DIALKYLNAPHTHALENE

BACKGROUND OF THE INVENTION

1. Field of the Invention

The present invention relates to a method for preparing dialkylnaphthalenes from alkenylbenzene compounds as a starting material. More particularly, the present invention relates to a method for preparing dialkylnaphthalenes by cyclizing and dehydrogenating alkenylbenzene compounds in one step.

2. Description of the Prior Art

Naphthalenedicarboxylic acids obtained by the oxidation of dialkylnaphthalenes are useful as a dibasic acid component for preparing polyesters. In particular, polyesters containing naphthalene-2,6-dicarboxylic acid as a dibasic acid component are well known to have excellent properties.

Roughly grouping, two methods have hitherto been known for the preparing of dialkylnaphthalenes. More specifically, there have been proposed a method which derives dialkylnaphthalene from naphthalene compounds, and a method which derives them from benzene compounds.

Examples of the method which uses naphthalene compounds as a starting material include methods in which naphthalenes are methylated (Japanese Patent Applications Laid-Open Nos. 45536/1985 and 172937/1985), a method in which naphthalenes are ethylated (Japanese Patent Applications Laid-Open Nos. 6953/1976 and 500179/1991 corresponding to U.S. Pat. No. 4,873,386), methods in which naphthalenes are propylated (WO90/03961, and Japanese Patent Applications Laid-Open Nos. 9942/1989 and 9943/1989), methods in which naphthalenes are acylated (Japanese Patent Applications Laid-Open Nos. 53937/1987, 188343/1985 and 135756/1979), and so on. These methods not only suffer from problems of impurities contained in the naphthalene compounds used as a raw material, and supply of purified naphthalenes, but also are less competitive from the viewpoint of cost.

On the other hand, the following methods have been proposed that derive dialkylnaphthalenes from alkylbenzenes. One is a method in which a starting material obtained by acylating alkylbenzene in the presence of a HF/BF$_3$ catalyst is subjected to a hydrogenating step, a dehydrating step and a cyclizing and dehydrogenating step to prepare a dialkylnaphthalene (Japanese Patent Applications Laid-Open Nos. 96540/1990 and 167237/1990). This method cannot be said to be advantageous industrially because of long procedure and use of a HF/BF$_3$ catalyst. Further, as the cyclizing and dehydrogenating catalyst, there have been proposed metal oxide catalysts such as alumina-chromia and iron oxide catalysts, or those catalysts containing precious metals such as platinum and palladium carried on alumina or activated carbon. There is cited $Cr_2O_3$—$K_2O$—$Al_2O_3$ as an example, which gives a very low selectivity for the objective compound.

Whereas a method has been known in which dimethylnaphthalene is obtained from a tolylpentene compound as a starting material by cyclization-dehydrogenation in one step. For example, U.S. Pat. No. 3,931,348 discloses use of a catalyst containing a combination of an alkali metal and chromia-alumina, a catalyst containing rhenium oxide, an alkali metal, and an alkaline earth metal carried on alumina, etc., as a cyclization-dehydrogenation catalyst. Their yields are too low to be industrially acceptable.

U.S. Pat. No. 3,244,758 suggests a method in which cyclization and dehydrogenation are performed simultaneously using platinum-alumina or platinum-silica alumina as a catalyst, without showing concrete data of actual reactions. Further, Japanese Patent Publication No. 1036/1975 describes a method in which the aforementioned one-step reaction is performed in a gas phase using a palladium catalyst. This method suffers from vigorous decomposition of the starting material and yield of dimethylnaphthalene, the objective compound, is low. Further, Japanese Patent Publication No. 1037/1975 described a method in which the aforementioned one-step reaction in a liquid phase using a silica alumina catalyst carrying thereon a metal such as platinum, palladium, rhodium or rhenium. This method, too, gives a low conversion of the starting material, and suffers from decomposition of the starting material, resulting in that it is unsuitable as an industrial process.

Also, a method has been proposed in which dimethylnaphthalene is prepared from xylenes and butadiene (Japanese Patent Publication Nos. 12430/1975 and 48494/1981). This method uses tolylpentenes obtained by alkenylating xylene with butadiene as a starting material and prepares dimethylnaphthalene compounds, the objective compounds, via a cyclizing step, a dehydrogenating step and a isomerizing step.

While this method is featured in that each reaction thereof has a very good selectivity and proceeds in a high yield, it is disadvantageous in that not only it involves a long series of steps but also it requires a complicated apparatus since the cyclizing step, which is an exothermic reaction, and the dehydrogenating step, which is an endothermic reaction, are independent of each other. Conventional proposals for carrying out these reactions in one step reaction have been unacceptable industrially as described above. In particular, alkenylbenzene compounds which are a starting material are susceptible to hydrogenation reaction, a side reaction, with hydrogen generated or carrier hydrogen and converted to alkylbenzene compounds. As a result, cyclization reaction is difficult to proceed, thus giving poor selectivity and yield.

SUMMARY OF THE INVENTION

A first object of the present invention is to provide an industrial process for obtaining dialkilnaphthalene directly from alkenylbenzene compounds which carries out cyclizing and dehydrogenating reaction in one step.

A second object of the present invention is to provide a method for preparing dialkilnaphthalene which carries out the aforementioned one step reaction at high selectivity.

Other object of the present invention is to provide a solid catalyst suitable for carrying out the aforementioned one step reaction on an industrial scale.

DETAILED DESCRIPTION OF THE INVENTION MEANS FOR SOLVING THE PROBLEMS

As a result of investigation by the present inventors, it has now been found that in a method for preparing a dialkylnaphthalene compound by contacting an alkenylbenzene compound represented by formula [A]

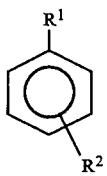

[A]

wherein $R^1$ is a butenyl group substituted with a $C_1$–$C_4$ alkyl group or a group —$CH_2$—$CH_2$—$CH_2$—$CH$=$CH$—$R^3$ (where $R^3$ is a hydrogen atom or a $C_1$–$C_4$ alkyl group), and $R^2$ is a $C_1$–$C_4$ alkyl group, with a solid catalyst in a gas or liquid phase at a temperature of 150° to 500° C. in the presence of hydrogen, use of the following composition (I) or (II) gives rise to a dialkylnaphthalene at a high conversion and a high selectivity.

Thus, it has been found that according to the present invention, the aforementioned object is achieved by use of the catalyst having the following composition (I) or (II).

Catalyst Composition (I)

This composition is represented by formula (I) below:

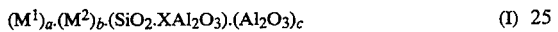
(I)

wherein $M^1$ represents at least one metal selected from the group consisting of metals belonging to group VIII of a periodic table and rhenium;

$M^2$ represents at least one member selected from the group consisting of zinc, gallium and oxides thereof;

X is a molar ratio of $Al_2O_3$ to $SiO_2$ in ($SiO_2.XAl_2O_3$) and is within the range of 0.05 to 5;

a is % by weight of $M^1$ based on the sum of ($SiO_2.XAl_2O_3$) and ($Al_2O_3)_c$, and is within the range of 0.01 to 5;

b is % by weight of $M^2$ as metal based on the weight of ($SiO_2.XAl_2O_3$), and is within the range of 0.1 to 50; and c is a weight ratio of ($Al_2O_3$) to ($SiO_2.XAl_2O_3$), and is within the range of 0 to 5.

Catalyst Composition (II)

This composition is represented by formula (II) below:

II-(i)

and

II-(ii)

wherein $M^3$ represents at least one metal belonging to group VIII of a periodical table;

d is % by weight of $M^3$ based on ($Al_2O_3$), and is within the range of 0.05 to 5;

$M^4$ represents at least one alkali metal;

e is % by weight of $M^4$ based on ($SiO_2.XAl_2O_3$), and is within the range of 0.05 to 10; and X is a molar ratio of $Al_2O_3$ to $SiO_2$ in ($SiO_2.XAl_2O_3$), and is within the range of 0.05 to 5.

Thus, according to the present invention, it is possible to carry out a cyclization reaction and a dehydrogenation reaction in one step reaction by contacting an alkenylbenzene compound represented by the aforementioned formula [A] with the aforementioned catalyst composition (I) or (II) in a gas or liquid phase, thus achieving a high conversion of the starting material and a high selectivity of the objective compound to obtain a dialkylnaphthalene in a high yield.

Hereinafter, the method of the present invention will be described in more detail.

In the method of the present invention, an alkenylbenzene compound represented by the aforementioned formula [A] is used as a starting material. In the aforementioned formula [A], the alkenylbenzene compound includes a benzene ring which has two substituents $R^1$ and $R^2$ thereon. $R^1$ is a butenyl group substituted with a $C_1$–$C_4$ alkyl group or a group —$CH_2$—$CH_2$—$CH_2$—$CH$=$C$—$R^3$ (where $R^3$ is a hydrogen atom or a $C_1$–$C_4$ alkyl group). Here, the aforementioned butenyl group is a group —$C^*H_2$—$C^*H_2$—$C^*H$=$CH_2$ of which any one $C^*$ among the three $C^*$'s is substituted with a $C_1$–$C_4$ alkyl group, preferably a methyl group. On the other hand, the substituent $R^2$ is a $C_1$–$C_4$ alkyl group, whose specific examples include a methyl group, an ethyl group, an n-propyl group, an isopropyl group, an n-butyl group, an isobutyl group, etc., with a methyl group being preferred.

The positions of the two substituents $R^1$ and $R^2$ may be any of ortho-, meta- and para-positions. The positions of $R^1$ and $R^2$ and the kind of the substituent on $R^1$ give a great influence on the position of the dialkyl group on the objective dialkylnaphthalene.

Specific examples of the alkenylbenzene compound represented by the aforementioned formula [A] include, for example, o-tolyl-2-methylbutene-3, o-tolyl-3-methylbutene-3, m-tolyl-2-methylbutene-3, m-tolyl-3-methylbutene-3, p-tolyl-2-methylbutene-3, p-tolyl-3-methylbutene-3, o-tolylpentene-3, o-tolylpentene-4, m-tolylpentene-3, m-tolylpentene-4, p-tolylpentene-3, p-tolylpentene-4, o-ethylphenyl-2-methylbutene-3, o-ethylphenyl-3-methylbutene-3, m-ethylphenyl-2-methylbutene-3, m-ethylphenyl-3-methylbutene-3, p-ethylphenyl-2-methylbutene-3, o-ethylphenylpentene-3, o-ethylphenylpentene-4, m-ethylphenylpentene-3, m-ethylphenylpentene-4, p-ethylphenylpentene-3, p-ethylphenylpentene-4, o-propylphenyl-2-methylbutene-3, o-propylphenyl-3-methylbutene-3, m-propylphenyl-2-methylbutene-3, m-propylphenyl-3-methylbutene-3, p-propylphenyl-2-methylbutene-3, p-propylphenyl-3-methylbutene-3, o-propylphenylpentene-3, o-propylphenylpentene-4, m-propylphenylpentene-3, m-propylphenylpentene-4, p-propylphenylpentene-3, p-propylphenylpentene-4, o-tolyl-2-ethylbutene-3, m-tolylethylbutene-3, p-tolyl-2-ethylbutene-3, o-tolyl-3-ethylbutene-3, m-tolyl-3-ethylbutene-3, p-tolyl-3-ethylbutene-3, o-tolylhexene-3, o-tolylhexene-4, m-tolylhexene-3, m-tolylhexene-4, m-tolylhexene-5, p-tolylhexene-3, p-tolylhexene-4, p-tolylhexene-5, etc.

As described above, the kinds of the substituents $R^1$ and $R^2$ and bonding positions of $R^1$ and $R^2$ of the alkenylbenzene compound give an influence on the kind of the dialkylnaphthalene obtained as a result of the reaction. To take some preferred examples thereof, there are prepared mainly 2,7-dimethylnaphthalene when m-tolyl-2-methylbutene-2 or -3 is used as a starting material; 2,6-dimethylnaphthalene in the case of m-tolyl-3-methylbutene-2 or -3, and p-tolyl-2-methylbutene-2 or -3; 1,5-dimethylnaphthalene in the case of o-tolylpentene-2, -3 or -4; 1,6-dimethylnaphthalene in the case of o-tolyl-3-methylbutene-2 or -3; 1,7-dimethylnaphthalene in the case of o-tolyl-2-methylbutene-2 or -3.

Among the aforementioned alkenylbenzene compounds, o-tolylpentene-2, -3, or -4 is preferred in view of availability and type of the objective dimethylnaphthalene.

In the method of the present invention, a dialkylnaphthalene is prepared by a one step reaction in which an alkenylbenzene compound represented by the aforementioned formula [A] is contacted with the aforementioned catalyst composition (I) or (II). Therefore, these catalysts used in the method of the present invention are multifunctional catalysts which have a cyclization function which forms a dialkyltetraline compound from an alkenylbenzene compound, and a dehydrogenation function which converts the tetraline compound into a dialkylnaphthalene compound under the same reaction conditions. In addition, the aforementioned catalysts used in the method of the present invention retain the aforementioned desired functions for a long time without causing any side reactions such as hydrogenation of alkenyl groups in the starting material under hydrogen atmosphere conditions.

Next, the catalyst compositions (I) and (II), and their preparation will be described concretely.

(1) Catalyst Composition (I) and Its Preparation

Catalyst composition (I) is represented by formula (I) below as described above.

$$(M^1)_a \cdot (M^2)_b \cdot (SiO_2 \cdot XAl_2O_3) \cdot (Al_2O_3)_c \qquad (I)$$

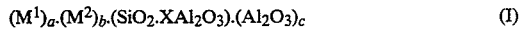

In short, the aforementioned composition (I) can be said to be a solid catalyst composed of silica-alumina represented by $(SiO_2 \cdot XAl_2O_3)$ having carried thereon $M^1$ and $M^2$ components, and optionally alumina represented by $(Al_2O_3)_c$ mixed therewith $M^1$ is at least one metal selected from the group consisting of group VIII metals of a periodical table and rhenium. More specifically, there can be cited Pt (platinum), Pd (palladium), Rh (rhodium), Ru (ruthenium), Os (osmium), Ir (iridium) or Re (rhenium). These may be used singly or in admixture.

Among them, preferred are/is Pt (platinum) and/or Re (rhenium).

$M^2$ is at least one metal selected from the group consisting of zinc (Zn) and gallium (Ga), or its oxide.

In the aforementioned composition (I), $(SiO_2 \cdot XAl_2O_3)$ is a silica-alumina component, and X is a molar ratio of $Al_2O_3$ to $SiO_2$, which is within the range of 0.05 to 5, and preferably 0.1 to 3.

The proportion (a) of the $M^1$ component is within the range of 0.01 to 5% by weight, and preferably 0.1 to 3% by weight based on the sum of $(SiO_2 \cdot XAl_2O_3)$ and $(Al_2O_3)$.

The proportion (b) of the $M^2$ component is within the range of 0.1 to 50% by weight, and preferably 1 to 40% by weight, as metal, based on the weight of $(SiO_2 \cdot XAl_2O_3)$.

The proportion (c) of alumina $(Al_2O_3)$ is within the range of 0 to 5 parts by weight, and preferably 0.2 to 4 parts by weight per part by weight of silica-alumina component $(SiO_2 \cdot XAl_2O_3)$. The alumina $(Al_2O_3)$ is in the form of a mixture with $(M^1)_a \cdot (M^2)_b \cdot (SiO_2 \cdot XAl_2O_3) \cdot (Al_2O_3)_c$, and also serves as a diluent or binder (modling aid). On the other hand, as another embodiment, the catalyst composition (I) may also be a solid catalyst in the form of a mixture of alumina $(Al_2O_3)$ having carried thereon a portion or all of the $M^1$ component, and $(M^2)_b \cdot (SiO_2 \cdot XAl_2O_3)$. This solid catalyst is included in the catalyst composition (I) of the present invention so far as it has the aforementioned composition.

The aforementioned catalyst composition (I) can be prepared by the following method. That is, an aqueous solution of salt(s) of zinc (Zn) and/or gallium (Ga) and silica-alumina $(SiO_2 \cdot XAl_2O_3)$ powder are mixed, and the salt(s) is/are carried on the silica-alumina by evaporation to dryness or dipping and filtration, and then the calcined to obtain silica-alumina having carried thereon zinc and/or gallium oxide(s). Next, the silica-alumina thus obtained and an aqueous solution of a compound of the metal in the $M^1$ component are mixed, and calcined at a temperature of, for example, 450° to 500° C. so that an oxide of the metal in the $M^1$ component is carried on the aforementioned silica-alumina (which carries thereon the $M^2$ component). The powder thus obtained may be molded as it is, or mixed with alumina $(Al_2O_3)$ and molded into granules or pellets. The molded catalyst may be further calcined, or reduced in a hydrogen atmosphere before use to exhibit its activity.

As the salt of zinc (Zn) to be introduced into the $M^2$ component used in the preparation of the aforementioned catalyst composition (I), are preferred those which are water-soluble and can be converted into zinc oxide under calcination conditions. For example, there can be cited zinc nitrate, zinc chloride, zinc acetate, etc. As the salt of gallium, are preferred similarly those which are water-soluble and can be converted into gallium oxide under calcination conditions. For example, there can be cited gallium nitrate, gallium chloride, gallium acetate, etc. The salts of zinc and those of gallium may be used singly or as mixture.

On the other hand, as the at least one metal selected from the group consisting of metals belonging to group VIII of a periodical table and rhenium, are preferred those which are water-soluble and can be converted into an oxide under calcination conditions. For example, chlorides, nitrates, or acetates of the aforementioned metals can be used.

(2) Catalyst Composition (II) and Its Preparation:

Catalyst composition (II) is a mixture of the following formula II-(i) and II-(ii):

$$(M^3)_d \cdot (Al_2O_3) \qquad \text{II-(i)}$$

$$(M^4)_e \cdot (SiO_2 \cdot XAl_2O_3) \qquad \text{II-(ii)}$$

The above-described formula II-(i) represents alumina $(Al_2O_3)$ on which the $M^3$ component is carried. $M^3$ represents at least one metal belonging to group VIII of a periodical table. Specifically Pt (platinum), Pd (palladium) and Rh (rhodium) are preferred, with Pt (platinum) being particularly preferred. The proportion (d) of $M^3$ is within the range of 0.05 to 5% by weight, and preferably 0.1 to 3% by weight based on alumina $(Al_2O_3)$.

The above-described formula II-(ii) represents silica-alumina $(SiO_2 \cdot XAl_2O_3)$ which includes an alkali metal $(M^4)$ being ion exchanged or carried thereon. As the alkali metal $(M^4)$, are preferred Na (sodium) and K (potassium), with Na (sodium) being particularly preferred. The proportion (e) of $M^4$ is within the range of 0.05 to 10% by weight, and preferably 0.1 to 5% by weight. On the other hand, X in the silica-alumina represents a molar ratio of $Al_2O_3$ to $SiO_2$, and is within the range of 0.05 to 3, and preferably 0.1 to 3.

The aforementioned catalyst composition (II) is a mixture of the above formulae II-(i) and II-(ii) as described above, and is preferably a uniform mixture of the powder of II-(i) and the powder of II-(ii). The mixing proportion, by weight, of the two is within the range of 1:10 to 10:1, and preferably 1:5 to 5:1.

The aforementioned II-(i) can be prepared by impregnating alumina powder ($Al_2O_3$) with an aqueous solution of a compound of a metal in the $M^3$ component, having the compound of $M^3$ carried on the alumina ($Al_2O_3$) by evaporation to dryness or dipping and filtration, and calcining it. This calcination may be carried out at a temperature of 400° to 500° C., or may be performed after the mixing with the component II-(ii). As the compound of $M^3$ to be used, those compounds are suitable which are water-soluble compounds of group VIII metals and can form oxides by calcination. For example, chlorides and nitrates are preferred.

On the other hand, the aforementioned II-(ii) can be prepared by impregnating silica-alumina powder ($SiO_2.XAl_2O_3$) with an aqueous solution of a compound of a metal in the $M^4$ component, having the compound $M^4$ carried on the silica-alumina ($SiO_2.XAl_2O_3$) by evaporation to dryness or dipping and filtration, and calcining it. This calcination may be carried out at a temperature of 400° to 500° C. or may be performed after the mixing with the component II-(i). As the compound of $M^4$ to be used for the preparation of II-(ii), those compounds are preferred which are water-soluble and can form oxides upon calcination. For example, chlorides, hydroxides or nitrates are preferred.

The catalyst composition (II) can be prepared by mixing the powders II-(i) and II-(ii) obtained as described above in the aforementioned proportions. The catalyst composition (II) may be supplied to the reaction after the powder mixture is molded into granules or pellets by a process known per se. To do so is preferred.

The catalyst compositions (I) and (II) of the present invention described above each are novel as catalysts for cyclizaiton.dehydrogenation, and the use of them as catalysts in reaction methods and under reaction conditions described below can give rise to dialkylnaphthalenes in high yields. Also, a specified dialkylnaphthalene can be obtained at a high selectivity.

III. Reaction method and Conditions Thereof:

In the method of the present invention, the reaction is carried out by contacting the alkenylbenzene compound of the aforementioned formula [A] as a starting material with the aforementioned catalyst composition (I) or (II) in a hydrogen atmosphere. In this case, the reaction may be carried out either in a gas phase reaction in which the starting material is contacted with the catalyst in the form of vapor, or in a liquid phase reaction in which the starting material is contacted with the catalyst in the form of a liquid. In the both gas phase reaction and liquid phase reaction, the catalyst may be of an type such as a fixed bed type, a mobile bed type, a fluidized bed type, or a suspension type. Further, the reaction may be a continuous type, batch type, or the like.

The reaction temperature is 150° C. to 500° C., and preferably 200° C. to 450° C., and the reaction pressure may be either atmospheric or superatmospheric. In a liquid phase reaction, the reaction may be carried out under pressure so that the alkenylbenzene compound as a starting material can be retained in the form of a liquid.

Upon the reaction, the starting material may be diluted with another stable diluent. For example, there can be used organic diluents, e.g., benzene compounds such as benzene, toluene, and xylene; naphthalene derivative compounds such as naphthalene, alkylnaphthalene, tetraline, alkyltetraline, decaline, alkyldecalines; and further inorganic diluents, e.g., gases such as nitrogen. In order to increase yield, and prevent deactivation of the catalyst, hydrogen gas is made present. When the starting material of the reaction is diluted, molar proportion of the diluent/starting material of the reaction 0.5 to 30, and preferably 1 to 15. WHSV, which is a contact time during which the starting material contacts the catalyst, is 0.1 to 20, and preferably 0.2 to 10.

EFFECT OF THE INVENTION

According to the present invention, reaction of a specified alkenylbenzene compound using a specified catalyst prepares a dialkylnaphthalene, and therefore a specified dialkylnaphthalene can be obtained at a high selectivity and in a high yield. Further, the reaction which has been carried out in two steps conventionally can be performed in one step, and hence the method of the present invention is economically excellent.

In particular, the method of the present invention is excellent in that a specified dialkylnaphthalene aimed at can be obtained at a very high selectivity. Hereinafter, this advantage will be described in more detail.

Dialkyltetraline, which are products of the cyclization reaction derived from alkenylbenzene compounds and intermediate products in the method of the present invention, can isomerize freely on acid catalysts and give rise to various isomers. Once they are dehydrogenated and converted into dialkylnaphthalenes, they are classified into four groups as shown in the following table. While isomerization reactions can readily occur between iosmers within each groups, generally isomerization reactions between groups are difficult to occur.

| No. | Group | Isomer |
| --- | --- | --- |
| 1 | 2,3-Group | 1,4-, 1,3-, 2,3-Dialkylnaphthalenes |
| 2 | 1,6-Group | 1,5-, 1,6-, 2,6-Dialkylnaphthalenes |
| 3 | 2,7-Group | 1,8-, 1,7-, 2,7-Dialkylnaphthalenes |
| 4 | Others | 1,2-Dialkylnaphthalene |

Therefore, in the method for preparing an objective dimethylnaphthalene compound from an alkenylbenzene compound which is obtained by alkenylation of xylenes with butadiene as a starting material by a cyclizing step, a dehydrogenating step, and an isomerizing step, it is important that the reaction product in the dehydrogenating step is a specified dimethylnaphthalene or that belonging to a specified group since it is only necessary to proceed isomerization reactions between those isomers that are included in each selected group to proceed, that is those reactions which can take place readily in the subsequent isomerization step. In the case where the cyclizing step, which is an exothermic reaction, and the hydrogenating step, which is an endothermic reaction, are practiced in a one-step reaction, it is similarly important to proceed the dehydrogenation reaction efficiently while suppressing the isomerization reaction of dialkyltetraline produced by the cyclization reaction in order to obtain the objective dialkylnaphthalene compound.

The use of the catalyst compositions (I) and (II), in particular composition (II), in the method of the present invention substantially suppresses the isomerization reaction of dialkyltetraline, intermediate product of the reaction, resulting in that dialkylnaphthalene of a specified group can be obtained at a high conversion and a high selectivity. For example, dialkylnaphthalenes of 2,6-group are preferred as a starting material for 2,6-naphthalenedicarboxylic acid. For this purpose, for example; mainly 2,6-dimethylnaphthalene is obtained from m-tolyl-3-methylbutene-2 or -3, and p-tolyl-2-methylbutene-2 or -3, mainly 1,5-dimethylnaphthalene from o-tolylpentene-2, -3 or -4; and mainly 1,6-dimethylnaphthalene is obtained from o-tolyl-3-methylbutene-2 or -3.

Preparation of Dialkyltetralines

According to another investigation by the present inventors, there has been found the following method for preparing a dialkyltetraline from the alkenylbenzene compound represented by the aforementioned formula [A] at a high conversion and a high selectivity. The dialkyltetraline thus obtained can readily be converted into a dialkylnaphthalene by contacting it with a dehydrogenating catalyst.

That is, according to the present invention, there is provided a method for preparing a dialkyltetraline compound by contacting an alkenylbenzene compound represented by formula [A] below:

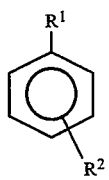

[A]

wherein $R^1$ is a butenyl group substituted with a $C_1$-$C_4$ alkyl group or a group $-CH_2-CH_2-CH_2-CH=CH-R^3$ (where $R^3$ is a hydrogen atom or a $C_1$-$C_4$ alkyl group), and $R^2$ is a $C_1$-$C_4$ alkyl group, with a solid catalyst in a gas or liquid phase at a temperature of 200° to 500° C. substantially in the absence of hydrogen, wherein as said solid catalyst is used a catalyst having a composition represented by formula (III) below:

$$M^5 f.(SiO_2.XAl_2O_3) \quad (III)$$

where $M^5$ represents at least one metal selected from the group consisting of alkali metals, zinc, gallium and oxides thereof;

f is % by weight of $M^5$ as metal based on ($SiO_2.XAl_2O_3$), and is within the range of 0.01 to 50; and X is a molar ratio of $Al_2O_3$ to $SiO_2$ in ($SiO_2.XAl_2O_3$), and is within the range of 0.05 to 5.

In the aforementioned method, the alkenylbenzene compound represented by formula [A] and used as starting material may be the same as that described the preparation of the aforementioned dialkylnaphthalene. Preferred starting material may be the same as that described above as preferred ones.

Referring to the solid catalyst having the composition represented by formula (III) used in the aforementioned method, this is a catalyst which contains silica-alumina ($SiO_2.XAl_2O_3$) having carried thereon the $M^5$ component. In the composition (III), $M^5$ is at least one metal selected from the group consisting of alkali metals, zinc and gallium, and oxides thereof. As the alkali metal, sodium or potassium is preferred. f is % by weight of $M^5$ as metal based on the silica-alumina ($SiO_2.XAl_2O_3$), and is within the range of 0.01 to 50% by weight, and preferably 0.1 to 40% by weight. Most preferred range of f is 0.1 to 30% by weight when $M^5$ is an alkali metal, and 1 to 40% by weight when $M^5$ is zinc, gallium or their oxides. X of the silica-alumina ($SiO_2.XAl_2O_3$) is a molar ratio of $Al_2O_3$ to $SiO_2$, and is within the range of 0.05 to 5, and preferably 0.1 to 3.

The composition (III) can be prepared by mixing an aqueous solution of a compound of the metal in the $M^5$ component with a silica-alumina powder ($SiO_2.XAl_2O_3$), subjecting the mixture to evaporation to dryness or dipping filtration to have the salt of the metal in the $M^5$ component carried on the silica-alumina, and then calcining. The calcination is performed suitably at a temperature of 450° to 500° C. As the salt of the alkali metal used in the aforementioned preparation, there can be cited, for example, sodium hydroxide, potassium hydroxide, etc. As the salt of zinc or gallium, there can be cited, for example, zinc nitrate, zinc chloride, zinc acetate, gallium nitrate, gallium chloride, gallium acetate, etc.

The powder obtained by the aforementioned preparation method can be molded into granules or pellets by a suitable method. In this case, any method may be used as the molding method, or a molding aid may be used. That is, molded article obtained by mixing the above-described powder with a molding aid, molding and calcining may be used in the reaction. As the molding aid, there can be used clay, silica-alumina, boehmite, alumina, etc., with alumina being preferred. It is preferred that the molding aid be used in a weight proportion of 0.5 to 1.9 to the above-described catalyst.

The catalyst composition (III) obtained by the aforementioned preparation method is a novel catalyst composition as a catalyst for the preparation of a dialkyltetraline by cyclization of an alkenylbenzene compound.

The catalytic reaction of an alkenylbenzene compound using the catalyst composition (III) thus obtained may be carried out either in a gas phase reaction in which the starting material is contacted with the catalyst in the form of vapor, or in a liquid phase reaction in which the starting material is contacted with the catalyst in the form of a liquid. In the both gas phase reaction and liquid phase reaction, the catalyst may be of any type such as a fixed bed type, a mobile bed type, a fluidized bed type, or a suspension type. Further, the reaction may be a continuous type, batch type, or the like.

The reaction temperature is 200° C. to 500° C., and preferably 200° C. to 450° C., and the reaction pressure may be either atmospheric or superatmospheric. In a liquid phase reaction, the reaction may be carried out under pressure so that the alkenylbenzene compound as a starting material can be retained in the form of a liquid.

Upon the reaction, the starting material may be diluted with another stable diluent. For example, there can be used organic diluents, e.g., benzene compounds such as benzene, toluene, and xylene; and further inorganic diluents, e.g., gases such as nitrogen. When the starting material of the reaction is diluted, molar proportion of the diluent/starting material of the reaction is 0.5 to 30, and preferably 1 to 15. WHSV, which is a contact time during which the starting material of the reaction contacts the catalyst, is 0.1 to 20, and preferably 0.2 to 10.

The reaction of the present invention must be carried out substantially in the absence of hydrogen since in the presence of hydrogen no objective compound can be obtained.

According to the present invention, the cyclization reaction of an alkenylbenzene compound, which has been carried out using silica-alumina or the like catalyst at a low temperature (for example, at a temperature of 150° to 180° C.) in order to prevent side reactions, can be performed at a relatively high temperature and at a high selectively and in a high yield.

The dialkyltetraline thus obtained can be converted into a dialkylnaphthalene by a method known per se, for example, by a method in which it is contacted with a dehydrogenating catalyst, e.g., plantinum-alumina at a temperature of 300° to 500° C. to carry out dehydrogenation.

For example, in the case where 1,5-dimethyltetraline and/or 1,6-dimethyltetraline are/is reacted in a gas phase using a platinum-alumina catalyst to obtain 1,5-dimethylnaphthalene and/or 1,6-dimethylnaphthalene can be prepared efficiently by setting up the catalyst calcination temperature to 300° to 400° C., the catalyst reduction temperature to 400° to 500° C., and the reaction temperature to 350° to 450° C.; or the catalyst calcination temperature to 400° to 500° C., the catalyst reduction temperature to 300° to 400° C., and the reaction temperature to 350° to 450° C.

The present invention enables the cyclization reaction of alkenylbenzene compounds at substantially the same temperature range as that of the dehydrogenation reaction of dialkyltetralines, thus making it possible to carry out the cyclization reaction and dehydrogenation reaction at high energy efficiency without change in the reaction temperature.

Since a series of the cyclization and dehydrogenation reactions proceed in substantially the same temperature range, they can be carried out in the same reaction vessel or in respective reaction vessels, in a continuous process, a sequential process or in combination thereof.

EXAMPLES

Hereinafter, the present invention will be described in detail by examples.

Example 1

Preparation of Catalyst of Composition (I)

Powder (10 g) of silica-alumina catalyst (N631HN produced by Japan Gasoline Corporation, containing 28% by weight of $Al_2O_3$) was charged in 50 ml of deionized water containing 6.8 g of zinc nitrate hexahydrate while stirring, and stirred at 50° C. for 4 hours. Then, after it was evaporated to dryness using a rotary evaporator, the mixture was dried in an air atmosphere in an electric drier at 120° C. for one night. The powder obtained was calcined in an air atmosphere in a muffle furnace at 500° C. for 8 hours to prepare silica-alumina powder carrying thereon 15% zinc.

The above-described silica-alumina powder (5.75 g) carrying thereon 15% zinc was suspended in 50 ml of deionized water, to which was added 1 ml of an aqueous solution of chloroplatinic acid containing 5.75 mg of Pt, and the mixture was stirred at 50° C. for 4 hours. Then, after it was evaporated to dryness using a rotary evaporator, the mixture was dried in an air atmosphere in an electric drier at 120° C. for one night. The powder obtained was calcined in an air atmosphere in a muffle furnace at 500° C. for 8 hours, and thereafter, the same weight of γ-alumina was well mixed therewith. The resulting mixture was molded into pellets with adjusting the grain size to 10 to 20 mesh to obtain catalyst A-1.

Catalyst A-1 contains 0.05% of platinum based on the total weight of the silica-alumina and alumina, and 15% of zinc based on the weight of the silica-alumina.

Similarly to the above-described catalyst A-1, catalysts A-2 to A-4 which contain platinum and zinc, catalysts B-1 to B-6 which contain group VIII metals other than platinum, or rhenium, and zinc, catalysts C-1 to C-6 which contain platinum and gallium, catalyst D-1 which contains rhenium and gallium, as shown in Table 1 were prepared.

Also, catalyst E which contains no metal, and catalyst F which contains only platinum were prepared similarly as described above as comparative catalysts.

Example 2

Evaluation of performances of Catalyst of Composition (I)

The catalyst (5 g) obtained as described above was precalcined in an air atmosphere in an electric furnace at 450° C. for 4 hours, and then filled in a reaction tube made of glass. After practicing reduction with hydrogen in a stream of hydrogen at 500° C. for 2 hours, the temperature was adjusted to a reaction temperature, and 10% toluene solution of a mixture of o-tolylpentene-3 and o-tolylpentene-4 was fed under the condition of WHSV=1. After 12 hours and 24 hours, respectively, from the supply of the oil, samples were collected, and analyzed by gas chromatography. Results obtained are shown in Table 1. (In Table 1, molar ratio means a molar ratio of carrier gas to starting material.)

Terms used in Table 1 are defined as follows:

Conversion =

$$\frac{\text{Amount of o-tolylpentene-3 or -4 converted (mole)}}{\text{Amount of o-tolylpentene-3 or -4 supplied (mole)}} \times 100$$

Loss Ratio =

$$\frac{\text{Amount of o-tolylpentene-3 or -4 formed (mole)}}{\text{Amount of o-tolylpentene-3 or -4 converted (mole)}} \times 100$$

Selectivity-1 =

$$\frac{\text{Amount of dimethyltetraline formed (mole)}}{\text{Amount of o-tolylpentene-3 or -4 converted (mole)}} \times 100$$

Selectivity-2 =

$$\frac{\text{Amount of dimethylnaphthalene formed (mole)}}{\text{Amount of o-tolylpentene-3 or -4 converted (mole)}} \times 100$$

TABLE 1

| Catalyst | Catalyst Composition | | Reaction Condition | | | Time of Oil Supply (hrs) |
|---|---|---|---|---|---|---|
| | $M^1$ (wt %) | $M^2$ (wt %) | Temperature (°C.) | WHSV ($hr^{-1}$) | Carrier, Molar Ratio | |
| A-1 | Pt, 0.05 | Zn, 15 | 450 | 1 | $H_2$, 4 | 12 |
| A-2 | Pt, 0.15 | Zn, 15 | 450 | 1 | $H_2$, 4 | 12 |
| A-3 | Pt, 0.25 | Zn, 15 | 450 | 1 | $H_2$, 4 | 12 |
| A-4 | Pt, 0.5 | Zn, 15 | 450 | 1 | $H_2$, 4 | 12 |
| A-4 | Pt, 0.5 | Zn, 15 | 450 | 1 | $H_2$, 4 | 24 |
| B-1 | Pd, 0.15 | Zn, 15 | 450 | 1 | $H_2$, 4 | 24 |

TABLE 1-continued

| Catalyst | | | | | | |
|---|---|---|---|---|---|---|
| B-2 | Rh, 0.15 | Zn, 15 | 450 | 1 | $H_2$, 4 | 24 |
| B-3 | Ru, 0.15 | Zn, 15 | 450 | 1 | $H_2$, 4 | 24 |
| B-4 | Os, 0.15 | Zn, 15 | 450 | 1 | $H_2$, 4 | 24 |
| B-5 | Ir, 0.15 | Zn, 15 | 450 | 1 | $H_2$, 4 | 24 |
| B-6 | Re, 0.15 | Zn, 15 | 450 | 1 | $H_2$, 4 | 24 |
| C-1 | Pt, 0.15 | Ga, 1 | 450 | 1 | $H_2$, 4 | 12 |
| C-2 | Pt, 0.15 | Ga, 3 | 450 | 1 | $H_2$, 4 | 12 |
| C-3 | Pt, 0.15 | Ga, 5 | 450 | 1 | $H_2$, 4 | 12 |
| C-4 | Pt, 0.15 | Ga, 10 | 450 | 1 | $H_2$, 4 | 12 |
| C-5 | Pt, 0.15 | Ga, 15 | 450 | 1 | $H_2$, 4 | 12 |
| C-5 | Pt, 0.15 | Ga, 15 | 450 | 1 | $H_2$, 4 | 12 |
| C-6 | Pt, 0.15 | Ga, 15 | 450 | 1 | $H_2$, 4 | 12 |
| D-1 | Re, 0.15 | Ga, 15 | 450 | 1 | $H_2$, 4 | 12 |
| Comparative E | — | — | 450 | 1 | $H_2$, 4 | 12 |
| Comparative F | Pt, 0.15 | — | 450 | 1 | $H_2$, 4 | 12 |

| Catalyst | Results of Reaction | | | | | | | |
|---|---|---|---|---|---|---|---|---|
| | Conversion (%) | Loss Ratio (%) | Selectivity-1 (%) | Selectivity-2 (%) | Distribution of Dialkylnaphthalene (%) | | | |
| | | | | | 2,3-Group | 2,6-Group | 2,7-Group | Others |
| A-1 | 100.0 | 1.0 | 4.6 | 91.7 | 1.7 | 80.1 | 18.2 | 0 |
| A-2 | 100.0 | 0.5 | 5.8 | 90.0 | 0.8 | 81.1 | 18.1 | 0.1 |
| A-3 | 100.0 | 0.6 | 3.7 | 94.1 | 1.6 | 80.5 | 17.8 | 0.1 |
| A-4 | 100.0 | 0.4 | 4.3 | 93.0 | 0.6 | 81.3 | 18.0 | 0.1 |
| A-4 | 100.0 | 1.0 | 3.8 | 90.5 | 0.5 | 81.0 | 18.5 | 0 |
| B-1 | 100.0 | 1.2 | 4.0 | 90.1 | 0.7 | 81.2 | 18.0 | 0.1 |
| B-2 | 100.0 | 0.2 | 7.4 | 89.4 | 0.0 | 82.0 | 17.9 | 0.1 |
| B-3 | 100.0 | 1.0 | 5.5 | 89.7 | 0.0 | 80.9 | 19.0 | 0.1 |
| B-4 | 100.0 | 1.2 | 4.4 | 89.9 | 2.0 | 80.0 | 18.0 | 0.0 |
| B-5 | 100.0 | 6.4 | 3.8 | 84.9 | 0.7 | 80.1 | 19.2 | 0.0 |
| B-6 | 100.0 | 0.9 | 5.0 | 89.8 | 0.2 | 80.3 | 19.5 | 0.0 |
| C-1 | 100.0 | 0 | 7.1 | 91.2 | 0.0 | 79.5 | 20.3 | 0.2 |
| C-2 | 100.0 | 0 | 6.0 | 90.0 | 0.1 | 80.3 | 19.5 | 0.1 |
| C-3 | 100.0 | 0 | 3.5 | 91.9 | 1.0 | 80.2 | 18.6 | 0.2 |
| C-4 | 100.0 | 0 | 3.3 | 92.0 | 0.9 | 82.0 | 17.0 | 0.1 |
| C-5 | 100.0 | 0.3 | 3.7 | 92.0 | 0.6 | 82.0 | 17.3 | 0.1 |
| C-5 | 100.0 | 0.4 | 4.0 | 90.8 | 0.4 | 83.0 | 16.5 | 0.1 |
| C-6 | 100.0 | 0 | 3.8 | 91.5 | 1.1 | 82.0 | 16.8 | 0.1 |
| D-1 | 100.0 | 0 | 4.1 | 91.7 | 0.8 | 80.9 | 18.2 | 0.1 |
| Comparative E | 100.0 | 19.2 | 2.9 | 40.4 | 1.7 | 69.5 | 28.7 | 0.1 |
| Comparative F | 95.4 | 43.0 | 7.3 | 6.4 | 1.0 | 70.0 | 29.0 | 0.0 |

Example 3

(Example in which o-tolyl-2-methylbutene-3 was used as alkenylbenzene compound)

Catalyst A-2 (5 g) in Example 1 above was filled in a reaction tube and subjected to reduction with hydrogen in the same manner as in Example 2 above. Thereafter, 10% toluene solution of o-tolyl-2-methylbutene-3 was fed WHSV=1 under the conditions of a reaction temperature of 450° C., and a hydrogen carrier/starting material molar ratio of 4. After 12 hours a sample was collected and analyzed by gas chromatography. As a result, the following performances were confirmed.

Conversion: 100.0%,
Loss ratio: 0.6%,
Selectivity-1: 7.0%,
Selectivity-2: 89.5%,
Dialkylnaphthalene distribution:
 2,3-group 1.0%
 2,6-group 18.3%
 2,7-group 80.6%
 Others 0.1%

Example 4

Preparation of Catalyst of Composition (II) Preparation of Composition II-(i)

γ-Alumina powder (ACP-1, produced by Shokubai Kasei Co., Ltd.) (50 g) was suspended in 200 ml of water, to which was charged 26.56 ml of an aqueous solution of chloroplatinic acid containing 7.53 mg of platinum/ml, and the resulting mixture was stirred at 50° to 60° C. for 5 hours. Then, after it was evaporated to dryness using a rotary evaporator, the mixture was dried in an air atmosphere in an electric drier at 120° C. for one night, and then at 200° C. for 3 hours.

Preparation of Composition II-(ii)

Powder (10 g) of silica-alumina catalyst (N631HN produced by Japan Gasoline Corporation, containing 28% by weight of $Al_2O_3$) was charged in 30 ml of deionized water containing 1.04 g of sodium hydroxide and stirred at 50° C. for 24 hours. Then, after it was filtered and washed with water, the content was dried in an air atmosphere in an electric drier at 120° C. for one night, and then calcined at 500° C. for 5 hours.

Preparation of Catalyst of Composition (II)

The powder of alumina carrying thereon platinum thus obtained and the powder of silica-alumina carrying sodium were mixed in a weight proportion of 2/1. After it was adjusted to 10 to 20 mesh, the resulting mixture was calcined at 450° C. for 8 hours to prepare catalyst G-1 which contained 0.4% of platinum and 2.3% of sodium.

In the same manner as the above-described catalyst, catalysts G-2 to G-8 were prepared which contained different group VIII metals and different alkali metals in different amounts as shown in Table 2.

Example 5

Evaluation of Performances of Catalyst of Composition (II)

Reactions were performed in the same manner as in Example 2, and results obtained are shown in Table 2. In Table 2, terms are the same as in Table 1.

As will be understood from Tables 1 and 2, according to the present invention, objective dialkylnaphthalene can be obtained in one step reaction in a high yield from o-tolylpentene-3 and -4 as starting material.

size was adjusted to 10 to 20 mesh to obtain catalyst H-1.

Catalysts H-2, H-3, and I-1 were prepared in the same manner as described above except that the amount of NaOH used was varied, or $K_2CO_3$ was used instead of NaOH.

The same silica-alumina powder (10 g) as used above was added to 50 ml of an aqueous solution containing 6.8 g of zinc nitrate hexahydrate, and the mixture was stirred at 50° C. for 4 hours.

Then, after it was evaporated to dryness, the mixture was dried in an air atmosphere in an electric drier at 120° C. for one night, the powder was calcined in an air atmosphere in a muffle furnace at 500° C. for 8 hours to prepare silica-alumina powder carrying 15% by weight of zinc. This was molded in the same manner as described above to obtain catalyst J-1.

Catalysts J-2 and J-3 were prepared by varying the amount of zinc nitrate used, and catalyst K-1 was prepared using silica-alumina powder containing 0.63% of Na, and further catalysts L-1 to L-3 were prepared using gallium chloride instead of zinc nitrate.

Example 7

TABLE 2

| | Catalyst Composition | | | Reaction Condition | | | |
|---|---|---|---|---|---|---|---|
| Catalyst | II-(1) $M^3$, wt % | II-(ii) $M^4$, wt % | Weight Proportion II-(i)/II-(ii) | Temperature (°C.) | WHSV ($hr^{-1}$) | Carrier, Molar Ratio | Time of Oil Supply (hrs) |
| G-1 | Pt, 0.4 | Na, 2.34 | 2 | 425 | 1 | $H_2$, 4 | 12 |
| G-2 | Pt, 0.4 | Na, 1.22 | 2 | 400 | 1 | $H_2$, 4 | 12 |
| G-3 | Pt, 0.4 | Na, 0.86 | 2 | 375 | 1 | $H_2$, 4 | 12 |
| G-4 | Pt, 0.4 | K, 0.17 | 2 | 400 | 1 | $H_2$, 4 | 12 |
| G-5 | Pt, 0.4 | Rb, 0.10 | 2 | 400 | 1 | $H_2$, 4 | 12 |
| G-6 | Pt, 0.4 | Cs, 1.84 | 2 | 400 | 1 | $H_2$, 4 | 12 |
| G-7 | Pt, 0.2 | Na, 0.49 | 2 | 400 | 1 | $H_2$, 4 | 12 |
| G-8 | Pt, 0.4 | Na, 0.86 | 2 | 350 | 1 | $H_2$, 4 | 12 |

| | | | | Results of Reaction | | | |
|---|---|---|---|---|---|---|---|
| Catalyst | Conversion (%) | Loss Ratio (%) | Selectivity-1 (%) | Selectivity-2 (%) | Distribution of Dialkylnaphthalene (%) | | |
| | | | | | 2,3-Group | 2,6-Group | 2,7-Group | Others |
| G-1 | 100.0 | 0.0 | 1.3 | 98.6 | 0.0 | 99.6 | 0.4 | 0.0 |
| G-2 | 100.0 | 0.0 | 1.3 | 98.6 | 0.0 | 99.6 | 0.4 | 0.0 |
| G-3 | 100.0 | 0.0 | 1.9 | 97.9 | 0.0 | 99.8 | 0.2 | 0.0 |
| G-4 | 97.5 | 0.3 | 3.7 | 90.0 | 0.5 | 92.2 | 7.3 | 0.0 |
| G-5 | 97.2 | 0.4 | 3.7 | 91.3 | 0.3 | 92.1 | 7.5 | 0.1 |
| G-6 | 96.9 | 0.4 | 3.7 | 90.7 | 0.4 | 92.4 | 7.1 | 0.1 |
| G-7 | 98.7 | 0.1 | 1.7 | 96.2 | 0.2 | 93.4 | 6.4 | 0.0 |
| G-8 | 100.0 | 0.0 | 1.3 | 98.6 | 0.0 | 99.8 | 0.2 | 0.0 |

Example 6

Preparation of Catalyst for Synthesis of Dialkyltetraline

Powder (10 g) of silica-alumina catalyst (N631HN produced by Japan Gasoline Corporation, containing 28% by weight of alumina) was charged in 100 ml of an aqueous solution containing 70 mmol of NaOH, and stirred at room temperature for 4 hours. Then, after it was filtered and well washed with 500 ml of deionized water, the powder was dried in an air atmosphere in an electric drier at 120° C. for one night. The powder obtained was calcined in an air atmosphere in a muffle furnace at 500° C. for 8 hours. As a result to analysis, this contained 1.91% by weight of Na based on silica-alumina powder.

The above-described silica-alumina powder containing Na was well mixed with the same weight of γ-alumina (Wako Pure Chemical Industry Co., Ltd. for chromatography), and molded into pellets, whose grain Evaluation of Performances of Catalyst for Synthesis of Dialkyltetralines The catalyst (5 g) obtained as described above was precalcined in an air atmosphere in an electric muffle furnace at 450° C. for 4 hours, and then filled in a reaction tube made of glass. The catalyst layer was adjusted to a reaction temperature, and 10% toluene solution of a mixture of o-tolylpentene-3 and o-tolylpentene-4 was fed at WHSV=1. After 12 hours from the supply of the oil, sample was collected, and analyzed by gas chromatography. Results obtained are shown in Table 3.

Catalyst E prepared in Example 1 was used as comparative catalyst.

Terms used in Table 3 are defined as follows:

Conversion (%) =

$$\frac{\text{Amount of o-tolylpentene-3 or -4 converted (mole)}}{\text{Amount of o-tolylpentene-3 or -4 supplied (mole)}} \times 100$$

Selectivity (%) =

$$\text{Selectivity (\%)} = \frac{\text{Amount of dimethyltetraline formed (mole)}}{\text{Amount of o-tolylpentene converted (mole)}} \times 100$$

TABLE 3

| Catalyst | Catalyst Composition $M^5$, wt % | Reaction Temperature (°C.) | Conversion (%) | Selectivity (%) |
|---|---|---|---|---|
| Comparative E | — | 200 | 100.0 | 86.3 |
| Comparative E | — | 250 | 100.0 | 80.1 |
| H-2 | Na, 0.63 | 200 | 100.0 | 95.7 |
| H-1 | Na, 1.91 | 200 | 98.5 | 96.3 |
| H-1 | Na, 1.91 | 250 | 100.0 | 94.1 |
| H-3 | Na, 3.81 | 250 | 93.9 | 97.5 |
| H-3 | Na, 3.81 | 350 | 100.0 | 91.4 |
| H-3 | Na, 3.81 | 450 | 100.0 | 89.8 |
| I-1 | K, 3.23 | 200 | 100.0 | 91.5 |
| J-2 | Zn, 5 | 200 | 100.0 | 93.5 |
| J-1 | Zn, 15 | 200 | 100.0 | 92.3 |
| J-1 | Zn, 15 | 250 | 100.0 | 89.6 |
| J-3 | Zn, 30 | 300 | 100.0 | 86.9 |
| K-1 | Zn, 15 Na, 0.63 | 300 | 100.0 | 95.6 |
| L-1 | Ga, 5 | 200 | 100.0 | 91.5 |
| L-2 | Ga, 15 | 200 | 100.0 | 89.3 |
| L-2 | Ga, 15 | 250 | 100.0 | 87.1 |
| L-3 | Ga, 30 | 300 | 100.0 | 85.6 |

Example 8

Dehydrogenation Reaction of Dialkyltetraline

Composition II-(i) prepared in Example 3 (alumina carrying 0.4% of platinum) was pulverized after molding to adjust the grain size to 10 to 20 mesh. This composition (5.0 g) was precalcined in an air atmosphere in an electric muffle furnace at 450° C. for 4 hours, and then filled in a reaction tube made of glass. After practicing reduction with hydrogen in a hydrogen stream at 400° C. for 2 hours, 10% toluene solution of 1,5-dimethyltetraline was fed at WHSV=1 hr$^{-1}$. The molar ratio of hydrogen gas/starting material supplied was 4. After 20 hours from the supply of the oil, product was collected, and analyzed. As a result, conversion was 98.5%, selectivity 91.5%, and yield 90.1%.

Terms used in Table are defined as follows:

$$\text{Conversion (\%)} = \left(1 - \frac{DMT_r \text{ (mol)}}{DMT_f \text{(mol)}}\right) \times 100$$

$$\text{Selectivity (\%)} = \frac{DMN \text{ formed (mol)}}{DMT_f - DMT_r \text{ (mol)}} \times 100$$

$$\text{Yield (\%)} = \frac{DMN \text{ formed (mol)}}{DMT_f \text{(mol)}} \times 100$$

where $DMT_r$ is 1,5-dimethyltetraline remaining in the dehydrogenation product;

$DMT_f$ is 1,5-dimethyltetraline fed to the reaction tube; and

DMN is 1,5-dimethylnaphthalene.

We claim:

1. A method for preparing a dialkylnaphthalene by contacting an alkenylbenzene compound represented by formula [A]

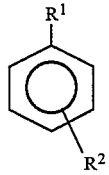

[A]

wherein $R^1$ is a butenyl group substituted with a $C_1$–$C_4$ alkyl group or a group —$CH_2$—$CH_2$—$CH_2$—$CH$=$CH$—$R^3$ (where $R^3$ is a hydrogen atom or a $C_1$–$C_4$ alkyl group), and $R^2$ is a $C_1$–$C_4$ alkyl group, with a solid catalyst in a gas or liquid phase at a temperature of 150° to 500° C. in the presence of hydrogen,
wherein as said solid catalyst is used a catalyst comprising a composition (I) or (II) below:
(1) Composition (I)

$$(M^1)_a \cdot (M^2)_b \cdot (SiO_2 \cdot XAl_2O_3) \cdot (Al_2O_3)_c \quad \text{(I)}$$

wherein $M^1$ represents at least one metal selected from the group consisting of metals belonging to group VIII of a periodic table and rhenium;
$M^2$ represents at least one member selected from the group consisting of zinc, gallium, and oxides thereof;
X is a molar ratio of $Al_2O_3$ to $SiO_2$ in ($SiO_2 \cdot XAl_2O_3$), and is within the range of 0.05 to 5;
a is % by weight of $M^1$ based on the sum of ($SiO_2 \cdot XAl_2O_3$) and ($Al_2O_3$)$_c$, and is within the range of 0.01 to 5;
b is % by weight of $M^2$ as metal based on the weight of ($SiO_2 \cdot XAl_2O_3$), and is within the range of 0.1 to 50;
c is weight ratio of ($Al_2O_3$) to ($SiO_2 \cdot XAl_2O_3$), and is within the range of 0 to 5.
(2) Mixture (II) (Mixture of II-(i) and II-(ii)):

$$(M^3)_d \cdot (Al_2O_3) \quad \text{II-(i)}$$

and $$(M^4)_e \cdot (SiO_2 \cdot XAl_2O_3) \quad \text{II-(ii)}$$

wherein $M^3$ represents at least one metal belonging to group VIII of a periodical table;
d is % by weight of $M^3$ based on ($Al_2O_3$), and is within the range of 0.05 to 5;
$M^4$ represents at least one alkali metal;
e is % by weight of $M^4$ based on ($SiO_2 \cdot XAl_2O_3$), and is within the range of 0.05 to 10; and
X is a molar ratio of $Al_2O_3$ to $SiO_2$ in ($SiO_2 \cdot XAl_2O_3$), and is within the range of 0.05 to 5.

2. The method as claimed in claim 1, wherein said $M^1$ is platinum.

3. The method as claimed in claim 1, wherein said $M^3$ is platinum.

4. The method as claimed in claim 1, wherein said $M^4$ is sodium or potassium.

5. The method as claimed in claim 1, wherein said X is within the range of 0.1 to 3.

6. The method as claimed in claim 1, wherein said a is within the range of 0.1 to 3.

7. The method as claimed in claim 1, wherein said b is within the range of 1 to 40.

8. The method as claimed in claim 1, wherein said c is within the range of 0.2 to 4.

9. The method as claimed in claim 1, wherein said d is within the range of 0.1 to 3.

10. The method as claimed in claim 1, wherein said e is within the range of 0.1 to 5.

11. The method as claimed in claim 1, wherein said mixture (II), said mixing proportion of formula II-(i) to formula II-(ii) is within the range of 1:10 to 10:1 by weight.

12. The method as claimed in claim 1, wherein said compound represented by said formula [A] is one in which $R^1$ is a butenyl group substituted with a methyl group or a group —$CH_2$—$CH_2$—$CH_2$—$CH$=$CH_2$, and $R^2$ is a methyl group.

13. The method as claimed in claim 1, wherein said compound represented by said formula [A] is an o-tolylpentene.

14. A method for preparing a dialkylnaphthalene by contacting an alkenylbenzene compound represented by formula [A]

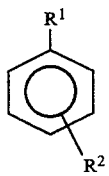

[A]

wherein $R^1$ is a butenyl group substituted with a $C_1$-$C_4$ alkyl group or a group —$CH_2$—$CH_2$—$CH_2$—$CH$=$CH$—$R^3$ (where $R^3$ is a hydrogen atom or a $C_1$-$C_4$ alkyl group), and $R^2$ is a $C_1$-$C_4$ alkyl group, with a solid catalyst in a gas or liquid phase at a temperature of 150° to 500° C. in the presence of hydrogen,
wherein as said solid catalyst is used a catalyst comprising a composition (I) below:

$$(M^1)_a \cdot (M^2)_b \cdot (SiO_2 \cdot XAl_2O_3) \cdot (Al_2O_3)_c \quad \text{(I)}$$

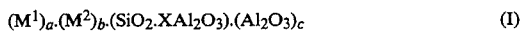

wherein $M^1$ represents at least one metal selected from the group consisting of metals belonging to group VIII of a periodic table and rhenium;
$M^2$ represents at least one member selected from the group consisting of zinc, gallium, and oxides thereof;
X is a molar ratio of $Al_2O_3$ to $SiO_2$ in $(SiO_2 \cdot XAl_2O_3)$, and is within the range of 0.05 to 5;
a is % by weight of $M^1$ based on the sum of $(SiO_2 \cdot XAl_2O_3)$ and $(Al_2O_3)_c$, and is within the range of 0.01 to 5;
b is % by weight of $M^2$ as metal based on the weight of $(SiO_2 \cdot XAl_2O_3)$, and is within the range of 0.1 to 50; and
c is weight ratio of $(Al_2O_3)$ to $(SiO_2 \cdot XAl_2O_3)$, and is within the range of 0 to 5.

15. The method as claimed in claim 14, wherein said $M^1$ is platinum.

16. The method as claimed in claim 14, wherein said X is within the range of 0.1 to 3.

17. The method as claimed in claim 14, wherein said a is within the range of 0.1 to 3.

18. The method as claimed in claim 14, wherein said b is within the range of 1 to 40.

19. The method as claimed in claim 14, wherein said c is within the range of 0.2 to 4.

20. The method as claimed in claim 14, wherein said compound represented by said formula [A] is one in which $R^1$ is a butenyl group substituted with a methyl group or a group —$CH_2$—$CH_2$—$CH_2$—$CH$=$CH_2$, and $R^2$ is a methyl group.

21. The method as claimed in claim 14, wherein said compound represented by said formula [A] is an o-tolylpentene.

22. A method for preparing a dialkylnaphthalene by contacting an alkenylbenzene compound represented by formula [A]

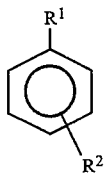

[A]

wherein $R^1$ is a butenyl group substituted with a $C_1$-$C_4$ alkyl group or a group —$CH_2$—$CH_2$—$CH_2$—$CH$=$CH$—$R^3$ (where $R^3$ is a hydrogen atom or a $C_1$-$C_4$ alkyl group), and $R^2$ is a $C_1$-$C_4$ alkyl group, with a solid catalyst in a gas or liquid phase at a temperature of 150° to 500° C. in the presence of hydrogen,
wherein as said solid catalyst is used a catalyst comprising a mixture of II-(i) and II-(ii) below:

$$(M^3)_d \cdot (Al_2O_3) \quad \text{II-(i)}$$

and $$(M^4)_e \cdot (SiO_2 \cdot XAl_2O_3) \quad \text{II-(ii)}$$

wherein $M^3$ represents at least one metal belonging to group VIII of a periodical table;
d is % by weight of $M^3$ based on $(Al_2O_3)$, and is within the range of 0.05 to 5;
$M^4$ represents at least one alkali metal;
e is % by weight of $M^4$ based on $(SiO_2 \cdot XAl_2O_3)$, and is within the range of 0.05 to 10; and
X is a molar ratio of $Al_2O_3$ to $SiO_2$ in $(SiO_2 \cdot XAl_2O_3)$, and is within the range of 0.05 to 5.

23. The method as claimed in claim 22, wherein said $M^3$ is platinum.

24. The method as claimed in claim 22, wherein said $M^4$ is sodium or potassium.

25. The method as claimed in claim 22, wherein said X is within the range of 0.1 to 3.

26. The method as claimed in claim 22, wherein said d is within the range of 0.1 to 3.

27. The method as claimed in claim 22, wherein said e is within the range of 0.1 to 5.

28. The method as claimed in claim 22, wherein said mixture (II), said mixing proportion of formula II-(i) to formula II-(ii) is within the range of 1:10 to 10:1 by weight.

29. The method as claimed in claim 22, wherein said compound represented by said formula [A] is one in which $R^1$ is a butenyl group substituted with a methyl group or a group —$CH_2$—$CH_2$—$CH_2$—$CH$=$CH_2$, and $R^2$ is a methyl group.

30. The method as claimed in claim 22, wherein said compound represented by said formula [A] is an o-tolylpentene.

* * * * *